United States Patent [19]

Baldwin et al.

[11] Patent Number: 4,788,193
[45] Date of Patent: Nov. 29, 1988

[54] 1-ARYLOXY-3-(SUBSTITUTED ALKYLAMINO)-2-PROPANOLS, PHARMACEUTICAL COMPOSITIONS AND USE

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 51,094

[22] Filed: May 18, 1987

Related U.S. Application Data

[62] Division of Ser. No. 600,693, Apr. 16, 1984.

[51] Int. Cl.[4] ............... A61K 31/495; A61K 31/535; C07D 295/14
[52] U.S. Cl. ................... 514/237.8; 514/253; 544/163; 544/401
[58] Field of Search ............... 544/163, 401; 514/237.8, 253

[56] References Cited

U.S. PATENT DOCUMENTS

| | | | |
|---|---|---|---|
| 2,943,090 | 6/1960 | Semb et al. | 544/401 |
| 3,332,997 | 7/1967 | Renner et al. | 544/401 |
| 4,191,765 | 3/1980 | Fritsch et al. | 544/401 |

Primary Examiner—Robert W. Ramsuer
Attorney, Agent, or Firm—Edward W. Murray; Michael C. Sudol

[57] ABSTRACT

The 1-aryloxy-3-(substituted alkylamino)-2-propanols of this invention and their pharmaceutically acceptable salts exhibit cardioselective β-adrenergic blocking activity, and are useful as antihypertensive, cardioprotective, antiarrhythmic and, antianginal agents.

6 Claims, No Drawings

1-ARYLOXY-3-(SUBSTITUTED ALKYLAMINO)-2-PROPANOLS, PHARMACEUTICAL COMPOSITIONS AND USE

CROSS REFERENCE TO RELATED APPLICATION

This is a divisional application to copending application Ser. No. 600,693, filed Apr. 16, 1984.

SUMMARY OF THE INVENTION

This invention is concerned with compounds of general structural formula I:

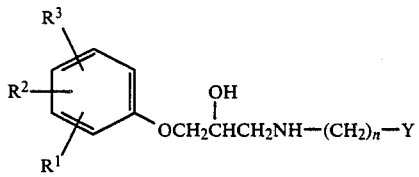

and pharmaceutically acceptable salts thereof wherein $R^1$, $R^2$, $R^3$, n and Y are as defined below.

These novel compounds and their pharmaceutically acceptable salts exhibit cardioselective β-adrenergic blocking activity, and are useful as antihypertensive, cardioprotective, antiarrhythmic, and antianginal agents; and are useful in the treatment of elevated intraocular pressure.

BACKGROUND OF THE INVENTION

A class of pharmaceutical agents known as β-adrenergic blocking agents, are available which affect cardiac, vascular and pulmonary functions and are mild antihypertensives. β-adrenergic blocking agents, their chemical structure and activity, are disclosed in *Clinical Pharmacology and Therapeutics*, 10, 292–306 (1969). Various β-adrenergic blocking agents are also described in the following patents: U.S. Pat. No. 3,048,387; U.S. Pat. No. 3,337,628; U.S. Pat. No. 3,655,663; U.S. Pat. No. 3,794,650; U.S. Pat. No. 3,832,470; U.S. Pat. No. 3,836,666; U.S. Pat. No. 3,850,945; U.S. Pat. No. 3,850,946; U.S. Pat. No. 3,850,947; U.S. Pat. No. 3,852,921; U.S. Pat. No. 4,115,575; U.S. Pat. No. 4,195,090; U.S. Pat. No. 4,115,575; U.S. Pat. No. 4,195,090; British Pat. No. 1,194,548; and South African Pat. No. 74/1070.

Now, with the present invention there are provided novel cardioselective β-blocking agents which have the capability of reducing heart rate, without counteracting vasodepression or suppressing bronchodilation; processes for their synthesis, pharmaceutical formulations comprising one or more of the novel compounds; and methods of treatment with the novel compounds or pharmaceutical compositions thereof wherein an antihypertensive, cardioprotective, antiarrhythmic or antianginal agent is indicated.

DETAILED DESCRIPTION OF THE INVENTION

The novel compounds of this invention are represented by the formula I:

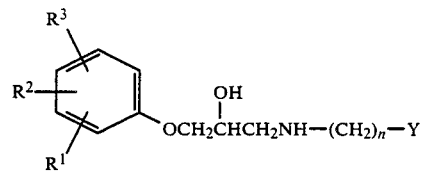

or a pharmaceutically acceptable salt thereof, wherein:

Y is
(1) a 6-membered heterocycle with 1 or 2 heteroatoms selected from O, N and S such as morpholino, piperazino, N-$C_{1-3}$ alkyl-piperazino, 2-, 3- or 4-pyridinyl, pyrimidinyl, pyrazinyl, or pyridazinyl, or
(2) di($C_{1-3}$ alkyl)amino;

$R^1$ is
(1) hydrogen,
(2) hydroxy, or
(3) hydroxymethyl;

$R^2$ and $R^3$ are independently:
(1) hydrogen,
(2) halo such as chloro, bromo or fluoro,
(3) hydroxy,
(4) amino,
(5) di($C_{1-5}$alkyl)amino,
(6) mono($C_{1-5}$alkyl)amino,
(7) nitro,
(8) cyano,
(9) $C_{1-6}$alkyl,
(10) $C_{3-8}$cycloalkyl,
(11) $C_{2-5}$alkenyl,
(12) $C_{1-4}$alkoxy,
(13) $C_{1-4}$ alkylthio,
(14) $C_{2-5}$alkenyloxy,
(15) $C_{1-5}$alkanoyl, such as formyl, pentanoyl or the like.

n=2, 3 or 4

In a preferred embodiment of the compound of this invention $R^1$ and $R^2$ are hydrogen, $R^3$ is cyano, and Y is morpholino, piperazino, N-($C_{1-3}$ alkyl)piperazino, pyrimidyl, pyrazinyl, 2-, 3-, or 4-pyridyl, pyridazinyl or dimethylamino; and n is 2.

The novel compounds of this invention include all the optical isomer forms as pure enantiomers or as mixtures containing the optical isomers such as racemic mixtures and compounds.

The compounds of the present invention also include the non-toxic pharmaceutically acceptable acid addition and quaternary ammonium salts. The acid addition salts are prepared by treating the compounds with an appropriate amount of a suitable organic or inorganic acid. Examples of useful organic acids are carboxylic acids such as maleic acid, tartaric acid, acetic acid, pamoic acid, oxalic acid, propionic acid, salicylic acid, succinic acid, citric acid, malic acid isethionic acid, and the like. Useful inorganic acids are hydrohalo acids such as hydrochloric, hydrobromic, hydriodic, sulfuric, phosphoric acid, or the like.

Compounds of the present invention may be prepared by any convenient method, however, the preferred methods utilized will depend upon the $R^1$, $R^2$, $R^3$, $R^4$ and Y groups. In the methods described below, the $R^1$–$R^4$ and Y groups are as defined above unless otherwise indicated. Also, unless otherwise indicated, the starting materials employed are known in the literature, are commercially available, or can be prepared by methods known to those skilled in the art.

METHOD A

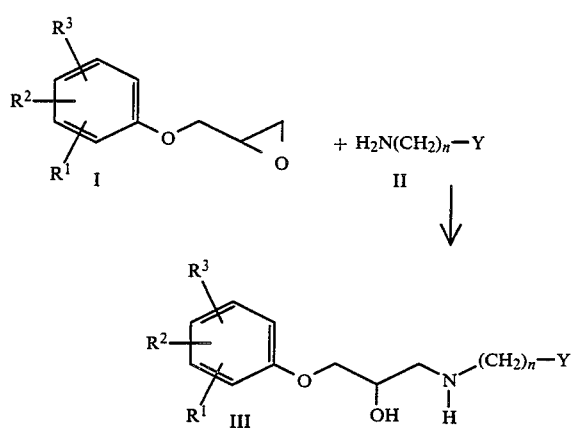

For Method A, an epoxide I is reacted with an appropriate amine, II in a suitable solvent such as methanol, ethanol, isopropanol, methylene chloride, THF or the like, at 0° C. to the reflux temperature of the solvent for about 1–48 hours, preferably in isopropanol at 45° C. for 18 hours, to yield III.

The novel compounds of this invention are active as cardioselective $\beta$-adrenergic receptor blocking agents and hence useful as antihypertensive, cardioprotective, antiarrhythmic, and antianginal agents, and useful in the treatment of elevated intraocular pressure.

For use as antihypertensives and/or $\beta$-adrenergic blocking agents, the present compounds can be administered transdermally, orally or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for parenteral administration; e.g., dissolved or dispersed in a suitable liquid carrier or emulsifier; or (c) as an aerosol or drug-impregnated patch for transdermal administration. Generally, doses of the novel compounds of from about 0.01 to about 50 mg/kg/day and preferably from about 0.1 to about 20 mg/kg of body weight per day are used. Dosage may be single or multiple depending on the daily total required and the unit dosage.

The in vitro $\beta$-adrenergic blocking properties of the novel compounds of this invention were evaluated in accordance with standard procedures. The interaction with the $\beta_1$-receptor was determined via inhibition of the positive chronotropic actions of isoproterenol in isolated guinea pig atrial preparations. $\beta_2$ potency was determined by using isolated guinea pig tracheal chains contracted with $PGF_{2@}$ and by measuring inhibition of isoproterenol-induced relaxation.

Typical results are shown in the following table.

| Y | pA$_2$ values $\beta_1$ (atria) | pA$_2$ values $\beta_2$ (trachea) | Cardioselectivity ratio |
|---|---|---|---|
| 3-pyridyl | 7.63 | 6.86 | 5.9 |
| 2-pyridyl | 7.46 | 4.46 | 1000 |
| 4-pyridyl | 7.13 | 6.52 | 4.1 |
| HN piperazinyl | 7.59 | 7.19 | 2.5 |
| O morpholinyl | 7.81 | 7.05 | 5.8 |
| —N(CH$_3$)$_2$ | 7.36 | 5.95 | 81.3 |

EXAMPLE 1

1-(2-Cyanophenoxy)3-[2-(4-pyridyl)ethyl]amino-2-propanol

Step A: Preparation of 3-(2-Cyanophenoxy)-1,2-epoxypropane

2-Cyanophenol (99.8 g, 0.84 mole) and epichlorohydrin (192 ml) in 2N NaOH (575 ml) were heated at 40° C. for 1½ hours. The reaction mixture was allowed to cool to room temperature and extracted with CHCl$_3$ (2×350 ml). The CHCl$_3$ extracts were combined, washed with H$_2$O (2×300 ml) and dried over Na$_2$SO$_4$. The CHCl$_3$ was removed in vacuo and the residue was crystallized twice from ether. The product was separated by filtration and dried in vacuo to yield 79 g (54%) of the desired epoxide, m.p. 65°–67°.

Step B: Preparation of 1-(2-Cyanophenoxy)-3-[2-(4-pyridyl)ethyl]amino-2-propanol The epoxide from Step A was dissolved in a mixture of 2-propanol (50 ml) and CH$_2$Cl$_2$ (20 ml) and added dropwise to a stirred solution of 4-(2-aminoethyl)pryidine (3.05 g, 25 mmole) in 2-propanol (4 ml) at 60° C. The reaction mixture was stirred at 60° C. for 6 hours then was allowed to cool to room temperature. The solvent was removed in vacuo and the product purified by chromatography on silica gel 60 (230–400 mesh). The column was eluted with 95-5-0.5 (CHCl$_3$—CH- 3OH—NH4OH v/v/v) to yield the product (3.3 g, 40%); m.p. 172° C.

Following the procedure substantially as described in Example 1 but substituting for 4-(2-aminoethyl)pyridine used in Step B thereof a corresponding amount of the amines of structure, H₂N-(CH₂)₂-Y described in Table II there are produced the 1-aryloxy-3-(substituted alkylamino)-2-propanols also described in Table II in accordance with the following reaction scheme:

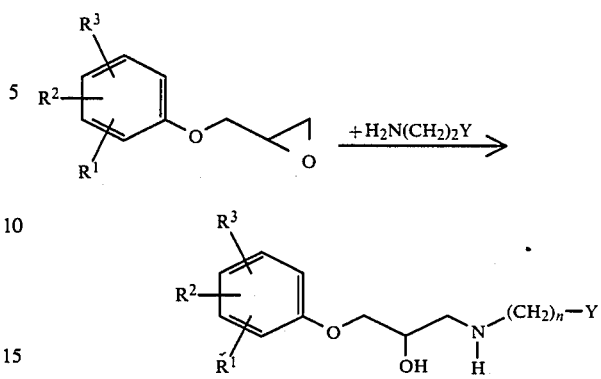

TABLE II

| R¹ | R² | R³ | n | Y | |
|---|---|---|---|---|---|
| H | H | 2-CN | 2 | 3-pyridyl | (m.p. 114–116° C. .2HCl) |
| H | H | 2-CN | 2 | 2-pyridyl | (m.p. 110–112° C. 2HCl.½H₂O) |
| H | H | 2-CN | 2 | —N(morpholino)O | (m.p. 173–5° C. 2HCl) |
| H | H | 2-CN | 2 | —N(piperazino)NH | (m.p. 249–51° C. 3HCl) |
| H | H | 2-CN | 2 | —N(CH₃)₂ | (m.p. 160–62° C.) |
| H | H | 2-F | 3 | pyrimidinyl | |
| 5-OH | H | H | 3 | pyrazinyl | |
| 5-HOCH₂— | H | H | 4 | pyridazinyl | |
| H | 4-OH | H | 4 | —N(morpholino)O | |
| H | H | 2-NH₂ | 3 | —N(piperazino)NH | |

TABLE II-continued

| R¹ | R² | R³ | n | Y |
|---|---|---|---|---|
| H | 3-N(CH₃)₂ | H | 4 | −N⌒N−CH₃ (N-methylpiperazinyl) |
| H | 3-CH₃ | 2-NHCH₃ | 2 | −N(CH₃)₂ |
| H | 4-NO₂ | 2-C₂H₅ | 3 | 2-methylpyrimidinyl |
| H | 3-OCH₃ | 2-CH₃ | 3 | 3-pyridyl |
| H | H | 2-C₂H₅ | 2 | 2-pyridyl |
| H | 3-n-C₃H₇ | H | 2 | morpholinyl (−N⌒O) |
| H | H | 2-n-C₆H₁₄ | 2 | piperazinyl (−N⌒NH) |
| H | 3-c-C₃H₅ | 2-CH₃ | 2 | −N⌒N−CH₃ |
| H | H | 2-c-C₆H₁₁ | 2 | −N(CH₃)₂ |
| H | 4-CH−CH=CH₂ | H | 2 | 4-pyridyl |
| H | H | 2-OCH₃ | 3 | 3-pyridyl |
| H | 3-O−CH(CH₃)₂ | H | 3 | 2-methylpyrimidinyl |
| H | H | 2-SC₂H₅ | 3 | morpholinyl |
| H | 4-O−CH=CHCH₃ (2) | H | 2 | piperazinyl (−N⌒NH) |

TABLE II-continued

| R¹ | R² | R³ | n | Y |
|---|---|---|---|---|
| H | H | 2-C(=O)-CH₃ | 2 | -N(CH₂CH₂)₂N-CH₃ (N-methylpiperazino) |
| H | 3-C(=O)-C₂H₅ | H | 2 | N-(CH₃)₂ |

| INGREDIENT | AMOUNT (Mg.) |
|---|---|
| TABLET FORMULATION I | |
| 1-(2-cyanophenoxy)-3-[2-(4-pyridyl)ethyl]amino-2-propanol | 40.0 |
| calcium phosphate | 120.0 |
| CAPSULE FORMULATION | |
| 1-(2-cyanophenoxy)-3-(2-piperazinylethyl)-amino-2-propanol trihydrochloride | 250 |
| lactose, U.S.P. | 93 |
| talc | 7 |
| INJECTABLE SOLUTION | |
| 1-(2-cyanophenoxy)-3-[2-(dimethylamino)ethyl]-amino-2-propanol | 5 |
| sodium chloride | 9 |
| distilled water, q.s. 1.0 ml. | |
| LIQUID SUSPENSION | |
| 1-(2-cyanophenoxy)-3-[2-(4-pyridyl)ethyl]amino-2-propanol | 5.0 |
| Veegum H.V. | 3.0 |
| methyl paraben | 1.0 |
| kaolin | 10.0 |
| glycerin | 250.0 |
| water, q.s. 1 liter | |

What is claimed is:

1. A compound of structural formula

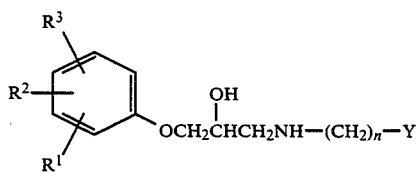

or a pharmaceutically acceptable salt thereof, wherein:
Y is a 6-membered nitrogen containing heterocycle selected from morpholino, piperazino or N-C₁₋₃ alkyl-piperazino;
R¹ is hydrogen;
R² is hydrogen;
R³ is cyano, and
n is 2, 3 or 4.

2. The compound of claim 1 or a pharmaceutically acceptable salt thereof wherein Y is piperazino; and n is 2.

3. A pharmaceutical β-blocking composition comprising a pharmaceutical carrier and an effective β-blocking amount of a compound of structural formula:

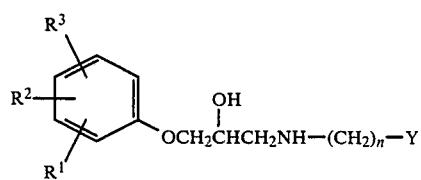

or a pharmaceutically acceptable salt thereof, wherein:
Y is A 6-membered nitrogen containing heterocycle selected from morpholino, piperazino or N-C₁₋₃alkyl-piperazino;
R¹ is hydrogen;
R² is hydrogen;
R³ is cyano, and
n is 2, 3 or 4.

4. The composition of claim 3 wherein Y is piperazino; and n is 2.

5. A method of treatment with a β-blocker which comprises the administration to a patient in need of such treatment of an effective β-blocking amount of a compound of structural formula:

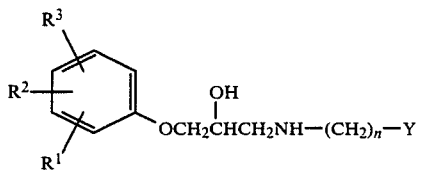

or a pharmaceutically acceptable salt thereof, wherein
Y is a 6-membered nitrogen containing heterocycle selected from morpholino, piperazino or N-C₁₋₃alkyl-piperazino;
R¹ is hydrogen;
R² is hydrogen;
R³ is cyano, and
n is 2, 3 or 4.

6. The method of treatment of claim 5 wherein Y is piperazino; and R is 2.

* * * * *